(12) United States Patent
Hosono et al.

(10) Patent No.: US 7,473,800 B2
(45) Date of Patent: Jan. 6, 2009

(54) METHOD OF MANUFACTURING ACETIC ACID

(75) Inventors: Yasuo Hosono, Yokohama (JP); Tadashi Matsumoto, Yokohama (JP); Rei Sato, Yokohama (JP); Takeshi Minami, Yokohama (JP); Chieko Nagasawa, Yokohama (JP); Munenori Maekawa, Yokohama (JP)

(73) Assignee: Chiyoda Corporation, Yokohama-shi (JP)

( * ) Notice: Subject to any disclaimer, the term of this patent is extended or adjusted under 35 U.S.C. 154(b) by 573 days.

(21) Appl. No.: 10/548,521

(22) PCT Filed: Mar. 11, 2004

(86) PCT No.: PCT/JP2004/003248

§ 371 (c)(1),
(2), (4) Date: Sep. 9, 2005

(87) PCT Pub. No.: WO2004/080941

PCT Pub. Date: Sep. 23, 2004

(65) Prior Publication Data

US 2006/0281944 A1 Dec. 14, 2006

(30) Foreign Application Priority Data

Mar. 13, 2003 (JP) ............................. 2003-067896
Mar. 31, 2003 (JP) ............................. 2003-094905
Mar. 31, 2003 (JP) ............................. 2003-095532

(51) Int. Cl.
*C07C 51/12* (2006.01)

(52) U.S. Cl. .................................................... 562/519

(58) Field of Classification Search ..................... None
See application file for complete search history.

(56) References Cited

U.S. PATENT DOCUMENTS

| 4,110,359 | A |   | 8/1978 | Marion |
| 5,508,442 | A | * | 4/1996 | Wagner et al. ............. 549/228 |
| 6,080,373 | A |   | 6/2000 | Uemura et al. |
| 6,521,783 | B1 |  | 2/2003 | Wegman et al. |

OTHER PUBLICATIONS

Yoneda et al, Applied Catalysis A: General, Recent Advances in Processes for the Production of Acetic Acid, 2001, 221, pp. 253-265.*
H. Gerstenberg, Verlag Chemic, GMBH, vol. 51, No. 3, 1979, pp. 208-216, XP009000370.

* cited by examiner

*Primary Examiner*—Paul A Zucker
(74) *Attorney, Agent, or Firm*—Westerman, Hattori, Daniels & Adrian, LLP.

(57) ABSTRACT

Acetic acid is manufactured by carbonylating methanol with carbon monoxide by way of a heterogeneous catalytic reaction in a bubble column reactor. The carbonylating reaction is conducted with a solid catalyst concentration of not less than 100 kg/m3 in terms of the reaction volume. For the reaction, the partial pressure of carbon monoxide in the reactor is confined to a range between 1.0 and 2.5 MPa while the exhaustion ratio of carbon monoxide is confined to a range between 3 and 15% of the theoretical reaction volume of carbon monoxide and the liquid superficial velocity is made to be found in a range between 0.2 and 1.0 m/sec.

21 Claims, 4 Drawing Sheets

METHOD OF MANUFACTURING ACETIC ACID

TECHNICAL FIELD

This invention relates to a method of manufacturing acetic acid. More particularly, the present invention relates to a method of manufacturing acetic acid by carbonylating methanol with carbon monoxide in a bubble column reactor in the presence of a solid catalyst, the reaction being conducted with a high catalyst concentration.

BACKGROUND ART

The so-called "Monsanto process" is well known for manufacturing acetic acid by causing methanol and carbon monoxide (CO) to react with each other in the presence of a noble metal catalyst. Originally, this method was developed to utilize a homogeneous catalytic reaction where methanol and carbon monoxide are caused to react with each other in a reaction solution prepared by dissolving a rhodium compound and methyl iodide respectively as metal catalyst and promotor in an acetic acid solvent that also contains water (Japanese Patent Publication No. 47-3334). A modified method was developed to utilize a heterogeneous catalytic reaction with use of a solid catalyst carrying a rhodium compound (Japanese Patent Application Laid-Open No. 63-253047). However, a homogeneous catalytic reaction is not adapted to a high rate of reaction because of the solubility of the catalyst metal is low relative to the solvent so that a large reactor may need to be used as a matter of course. Additionally, water need to be contained in the reaction solution to a certain ratio in order to increase the reaction rate and the selectivity for acetic acid and prevent deposition of the dissolved catalyst and consequently it gives rise to hydrolysis of methyl iodide that is contained as promotor to reduce the yield and corrode the reaction apparatus. For these and other reasons, a method utilizing a heterogeneous catalytic reaction has been developed because it is relatively free from such problems.

Carbonylation of methanol utilizing a heterogeneous catalytic reaction normally involves the use of acetic acid as solvent. More specifically, methanol and carbon monoxide are caused to react with each other under pressure and at high temperature in a reactor in the presence of a solid catalyst carrying a rhodium compound and a promotor of methyl iodide. The liquid reaction product extracted from the reactor is led to a separation system, which typically comprises a distillation means, in order to separate and collect the produced acetic acid, while the residual solution produced as a result of the separation is returned to the reactor. In this stage of operation, a two-phase system or a heterogeneous system exists in the reactor, in which the reaction solution contains acetic acid, methanol and methyl iodide as main components along with particles of the solid catalyst (a three-phase system containing bubbles of CO gas to be more accurate). Note that the reaction solution also contains methyl acetate, dimethyl ether, hydrogen iodide and water, which are reaction byproducts, in addition to the above listed main components. Particles of insoluble resin containing a pyridine ring in the molecular structure and carrying rhodium complex are normally used for the solid catalyst.

A continuous stirring tank reactor (CSTR) adapted to agitate the reaction solution by means of an impeller or a bubble column reactor adapted to agitate the reaction solution by means of bubbles may be used for the carbonylating reaction using a heterogeneous catalyst.

When using a continuous stirring tank reactor, particles of the solid catalyst are agitated and suspended in the reaction solvent and liquid methanol and CO gas are injected from the bottom as reaction raw materials and made to react with each other. Such a continuous stirring tank reactor, or agitation tank type suspension reactor, is accompanied by a problem of an enhanced rate of CO loss because the residence time of CO gas is relatively short in liquid and, once CO exits from liquid to move into the gas phase in the reactor, it can hardly be dissolved into liquid again. It is accompanied additionally by a problem of difficulty of separation of the catalyst and a reduced life span of the latter because it is structurally difficult to take out only the reacting solution from the reactor without allowing the solid catalyst to flow out of the rector and catalyst particles are encouraged to become finer particles by the stirrer.

To the contrary, a bubble column reactor is advantageous because it is free from the above listed problems and, since the reactor is cylindrical, CO gas passing through it can be made to show a long residence time. When such a bubble column reactor is used, the cylindrical reactor is filled with a reaction solvent and a solid catalyst and liquid methanol is supplied from the bottom as reaction raw material, while CO gas is injected upward from the bottom as jet stream. The injected CO gas forms bubbles as it rises in the liquid contained in the cylindrical reactor and particles of the catalyst are also driven to move upward in the cylindrical reactor by the gas lift effect and dispersed into the liquid. As a result, the carbonylating reaction proceeds. Then, the unreacted CO gas and the reaction solution that contains the solid catalyst are separated by a separator arranged at the top of the cylindrical reactor when they got to there. The unreacted CO gas is collected and part of the reaction solution is taken out from the top of the separator as liquid reaction product that does not contain any solid catalyst, while the remaining part of the reaction solution that contains the solid catalyst returns to the bottom of the cylindrical reactor by way of a circulation path by its own weight and is supplied once again to the cylindrical reactor to complete the circulation. With a known method of carbonylating reaction using such a bubble column reactor, CO gas is injected into the liquid contained in a cylindrical reactor as jet stream by way of a nozzle arranged at the bottom of the cylindrical reactor for the purpose of mobilizing particles of the solid catalyst in the reactor (Japanese Patent Application Laid-Open No. 6-340242).

More specifically, in the above reaction step, carbon monoxide is blown into the liquid reaction composition (containing particles of the solid catalyst in the case of a heterogeneous catalytic reaction) in the reactor and the gas phase components including unreacted carbon monoxide are drawn out from the top of the reactor as off gas. The liquid reaction composition that has reacted is separated from the particles of the solid catalyst and drawn out from the reactor so as to be led into a flash column or flash vessel. In the case of a flash column, carbon monoxide and gasified light-fraction components that have been dissolved in the liquid are separated as off gas by means of an operation of flash distillation and the residual liquid composition is divided into a crude acetic acid fraction that is to be refined to produce a final product of acetic acid by way of subsequent steps including a distillation step and a circulating fraction that is to be driven back into the reactor for circulation. In the case of a flash vessel, the liquid reaction composition is divided into a gaseous fraction containing components that correspond to the off gas and the crude acetic acid fraction mentioned above and a remaining liquid fraction, by means of an operation of flash evaporation, of which the gaseous fraction is refined in a subsequent distillation step and the liquid fraction is returned to the reactor. Off gas and a circulating fraction will be produced along with a refined acetic acid fraction, which is a final product, also in the subsequent steps including a distillation step.

As described above, in the process of manufacturing acetic acid, off gas is drawn out in each of the steps of the process including the reaction step and the subsequent steps of separation and refinement. The drawn out off gas contains not only methane and hydrogen that are produced as a result of reaction and unreacted carbon monoxide but also methyl iodide that is a promotor, acetic acid that is used as reaction raw material and reaction solvent and other gasified substances such as methyl acetate. Therefore, conventionally, these useful substances are collected and returned to the reactor before the off gas is burned in an incinerator. A gas absorption operation is generally employed to collect the useful substances from the off gas and the produced acetic acid or the raw material methanol is partly used as absorbent liquid for the gas absorption operation. When the produced acetic acid is partly employed as absorbent liquid, a diffusion step needs to be inevitably provided for the purpose of separating the useful substances absorbed into the acetic acid from the latter after using the latter as absorbent liquid. To the contrary, the use of part of the raw material methanol as absorbent liquid provides an advantage that the methanol that has been used as absorbent liquid can be introduced into the reactor without any treatment. Additionally, while any effort for cooling acetic acid to improve the absorption efficiency is baffled by the relatively high melting point (17° C.) of acetic acid, methanol is advantageous because it is not accompanied by such a problem.

DISCLOSURE OF THE INVENTION

When a heterogeneous reaction is conducted in a bubble column reactor by using a solid catalyst, moving particles of the solid catalyst can be highly probably blocked at the bottom of the cylindrical reactor when the concentration of particles of the solid catalyst is high, although such a problem does not arise so long as the concentration of particles of the solid catalyst remains low. Then, as reaction liquid containing the solid catalyst is driven toward the bottom of the cylindrical reactor for circulation by way of an external circulation path, the circulation path can be clogged by the deposited particles of the solid catalyst in the circulation path to give rise to a significant trouble to the operation. If the circulation path is not clogged, the solid catalyst can locally agglomerate to reduce the productivity of manufacturing acetic acid by way of the above described reaction process and promote side reactions.

Thus, known methods of manufacturing acetic acid by carbonylating methanol by means of a heterogeneous catalytic reaction, using a solid catalyst, are accompanied by problems including that they need to be conducted with a relatively low catalyst concentration and require the use of a large apparatus for carrying out the method when acetic acid has to be manufactured at a given rate. Therefore, it is an object of the present invention to provide a method of manufacturing acetic acid that is free from the problem of blocking moving particles of the solid catalyst in the reactor and clogging the circulation path due to the deposited particles of the solid catalyst so that the productivity of manufacturing acetic acid may not be reduced by local agglomeration of the solid catalyst and the operation of manufacturing acetic acid can be conducted reliably on a stable basis for a long period of time when a high catalyst concentration is used. It is also an object of the present invention to provide a reactor to be used with such a method.

Meanwhile, with a method according to the invention that involves a high catalyst concentration, the rate at which CO gas is blown in is also high and hence the rate at which off gas is produced is high if compared with known methods. As a gas absorption operation using raw material methanol as absorbent liquid is conducted to collect useful substances from off gas, the supply rate of methanol as absorbent liquid will increase as a matter of course. However, if methanol is used to absorb off gas at a rate higher than the rate at which raw material methanol is supplied to the reactor, the excessive methanol simply needs to be wasted because it cannot be utilized as raw material. Therefore, such a high supply rate of methanol is uneconomical. In other words, it is desirable that the rate at which methanol is used to absorb off gas is lower than the rate at which raw material methanol is supplied to the reactor. Thus, it will be appreciated that the efficiency of the off gas absorbing operation is vital to a method of manufacturing acetic acid when raw material methanol is used as absorbent liquid. Therefore, another object of the present invention is to raise the efficiency of the off gas absorbing operation.

According to the invention, there is provided a method of manufacturing acetic acid by carbonylating methanol with carbon monoxide (CO) by way of a heterogeneous catalytic reaction in a bubble column reactor, in which the carbonylating reaction is conducted with a solid catalyst concentration of not less than 100 kg/m$^3$ in terms of the reaction volume. The solid catalyst includes a catalyst metal complex supported on a particulate resin. The catalyst metal contains usually 0.3 to 2.0 wt %, preferably 0.6 to 1.0 wt %, of the particulate resin.

According to the invention, the productivity of the carbonylating reaction is improved when the solid catalyst concentration is not less than 100 kg/m$^3$ in terms of the volume of the reaction system so that a relatively small reactor can be used for the reaction to reduce the manufacturing cost. The solid catalyst concentration is the average catalyst concentration in both the reactor main body and the circulation system.

In an aspect of the present invention, with a method according to the invention where a solid catalyst concentration of not less than 100 kg/m$^3$ is used in terms of the volume of the reaction system, the partial pressure of carbon monoxide in the reactor is between 1.0 and 2.5 MPa and the exhaustion ratio of carbon monoxide is between 3 and 15% of the theoretical reaction volume of carbon monoxide, while the liquid superficial velocity is between 0.2 and 1.0 m/sec.

With such a high catalyst concentration, the partial pressure of carbon monoxide in the reactor is held within a range between 1.0 and 2.5 MPa, preferably between 1.7 and 2.2 Mpa, in order to maintain the mass transfer constant Kla (liquid phase capacity coefficient) of CO gas between gas and liquid, which is rate-controlling for the carbonylating reaction using CO, not less than a predetermined value (e.g., not less than 700). The overall productivity of the reaction remarkably falls when the partial pressure of carbon monoxide is not higher than 1.0, whereas the rate of reaction is not improved remarkably when the partial pressure of carbon monoxide exceeds 2.5 MPa. Thus, the overall reaction pressure can be held within an economical range between 1.5 and 5.9 MPa, preferably between 3.0 and 4.5 MPa when the partial pressure of carbon monoxide is held within the above defined range.

Carbon monoxide is supplied excessively to secure the sufficient Kla value and a value between 3 and 15%, preferably between 5 and 10%, is selected for the exhaustion rate of carbon monoxide (ratio of the excessive carbon monoxide relative to the theoretical reaction volume of carbon monoxide). While the Kla value improves remarkably when the exhaustion rate is not less than 3%, an exhaustion rate greater than 15% is not preferable from the economical point of view. As CO gas is supplied in excess, the gas lift effect is improved accordingly to serve for uniform fluidization of the solid catalyst.

Additionally, the liquid superficial velocity of reaction liquid that rises in the reactor is held between 0.2 and 1.0 m/sec in order to maintain a uniformly dispersed state of particles of the catalyst showing a high concentration so as to prevent the productivity of manufacturing acetic acid from falling and side reactions from being promoted due to localization of the solid catalyst caused by an insufficient circulation velocity. It is not preferable that the liquid superficial velocity is higher than 1.0 m/sec because the exhaust ratio of excessive CO gas rises and the residence time of CO gas becomes insufficient. Then, a remarkably high reactor may have to be installed to avoid such problems. If, on the other hand, the liquid superficial velocity of reaction liquid is lower than 0.2 m/sec, the catalyst will be distributed unevenly to increase localized reactions, which results in an increase of side reactions, and shorten the service life of the catalyst.

Similarly, the gas superficial velocity of CO gas is preferably between 2 and 8 cm/sec. The expression of gas superficial velocity as used herein refers to the average value of the gas superficial velocity in the gas lead-in section of the bottom of the reactor and the counterpart at the top of the reactor. When the gas superficial velocity is found within the above defined range, the solid catalyst is uniformly dispersed in the reactor due to such a velocity and the gas lift effect of CO gas rising in the reactor so that a necessary level of circulation/fluidization of the solid catalyst can be maintained on a stable basis.

The bubble column reactor to be used for manufacturing acetic acid by means of a heterogeneous reaction of carbonylation according to the invention preferably has a ratio of the length L to the diameter D, or L/D, of not smaller than 8 because it is required to provide a sufficiently long gas/liquid contact time and a sufficiently high level of circulation/fluidization in order to achieve a sufficient reaction efficiency. With a reactor having an L/D value of not smaller than 8, it is possible to establish a uniformly circulating flow of slurry of the solid catalyst at a rate not lower than the above mentioned 0.2 m/sec because the volume of the gaseous holdup in the reaction zone (riser section) increases to produce a sufficiently large density difference between the reaction zone and the liquid falling zone (down-comer section). While either the external circulation system or the internal circulation system may be used for the bubble column reactor, a heat exchanger is preferably incorporated in the circulation path in order to remove the heat generated by the reaction when the external circulation system is used.

In another aspect of the present invention, with a method according to the invention where a solid catalyst concentration of not less than 100 kg/m$^3$ is used in terms of the reaction volume, carbon monoxide is injected into the reactor by way of carbon monoxide blow-in ports arranged at a plurality of levels.

As carbon monoxide is injected into the reactor by way of carbon monoxide blow-in ports arranged at a plurality of levels, the solid catalyst in the reactor is fluidized and uniformized very efficiently if compared with a single level arrangement so that it is possible to operate the reaction system with a high solid catalyst concentration of not less than 100 kg/m$^3$. Then, it is possible to downsize the reactor.

The solid catalyst includes a catalyst metal complex supported on a particulate resin. The catalyst metal contains usually 0.3 to 2.0 wt %, preferably 0.6 to 1.0 wt %, of the particulate resin.

The solid catalyst in the reactor can be fluidized and uniformized even more efficiently when at least one of the carbon monoxide blow-in ports arranged at a plurality of levels is used as carbon monoxide blow-in port for fluidizing the solid catalyst and at least another one of the carbon monoxide blow-in ports arranged at a plurality of levels is used as carbon monoxide blow-in port for mobilizing the solid catalyst in a lower part of the reactor. When the carbon monoxide blow-in port for mobilizing the solid catalyst is arranged at the bottom of the reactor, the solid catalyst is prevented from depositing at the bottom of the reactor. When, on the other hand, the carbon monoxide blow-in port for fluidizing the solid catalyst is arranged at an appropriate position above the carbon monoxide blow-in port for mobilizing the solid catalyst, it is possible to move the catalyst upward in the reactor by the gas lift effect that arises when blown-in CO gas rises in the cylindrical reactor and disperse it in the liquid so as to efficiently fluidize the solid catalyst. While it is preferable to arrange at least a carbon monoxide blow-in port for fluidizing the solid catalyst and at least a carbon monoxide blow-in port for mobilizing the solid catalyst at respective levels, a plurality of blow-in ports may be arranged for fluidizing the solid catalyst and/or for mobilizing the solid catalyst whenever necessary.

When carbon monoxide blow-in ports are arranged at a plurality of levels in a manner as described above, it is possible to conduct the operation of manufacturing acetic acid reliably on a stable basis when the solid catalyst is used with such a high concentration that conventional bubble column reactors having one or more than one carbon monoxide blow-in ports arranged at a single level cannot handle. Particularly, the solid catalyst is effectively prevented from depositing and clogging the circulation path when the bubble column reactor is used with an external circulation system for circulating/supplying reaction liquid that contains the solid catalyst into a lower part of the reactor by way of an external circulation path and the carbon monoxide blow-in port for mobilizing the solid catalyst is arranged near the junction of the reactor and the external circulation path (i.e., circulation lead-in section) that is located at a lower part of reactor and apt to block the flow of particles of the solid catalyst.

In still another aspect of the present invention, there is provided a method of manufacturing acetic acid by carbonylating methanol with carbon monoxide in the presence of a solid metal catalyst, characterized in that it comprises:

a reaction step of causing a carbonylating reaction to take place by suspending the solid metal catalyst in a liquid reaction composition containing an organic solvent composed of methanol, methyl iodide, acetic acid and/or methyl acetate and water to a small content ratio and blowing carbon monoxide gas into the liquid reaction composition;

a first separation step of separating and taking out the liquid reaction composition and off gas from the reaction step;

a second separation step of conducting an operation of flash distillation by introducing the liquid reaction composition separated in the first separation step into a flash column and thereby separating off gas and a light liquid fraction flowing out from a tower top section, a crude acetic acid fraction flowing out from a tower middle section and a circulating fraction flowing out from a tower bottom section;

a third separation step of introducing part of the light liquid fraction and the crude acetic acid fraction separated in the second separation step into a distillation system and thereby separating off gas, a product acetic acid fraction, a heavy fraction and a circulating fraction;

a circulation step of returning the residue of the separated light liquid fraction and the circulating fraction separated in the second separation step and the circulating fraction separated in the third separation step to the reactor;

a first absorption step of conducting an operation of gas absorption for the off gas separated in the first separation step, using methanol as absorbent liquid;

a second absorption step of conducting an operation of gas absorption for the off gas separated in the second separation step and the off gas separated in the third separation step, using methanol as absorbent liquid under a pressure lower than that of the first absorption step; and an exhaustion step of exhausting the off gas left after the first absorption step, the off gas left after the second absorption step and the heavy fraction separated in the third separation step to the outside of the system; and that methanol that is regulated for temperature to 10 to 25° C. is used as absorbent liquid in the first and second absorption steps and divided so as to use 50 to 80 wt % of the entire methanol to be used in the two absorption steps in the second absorption step and the methanol left after the two absorption steps is used as raw material methanol in the reaction step.

In still another aspect of the invention, there is also provided a method of manufacturing acetic acid by carbonylating methanol with carbon monoxide in the presence of a solid metal catalyst, characterized in that it comprises:

a reaction step of causing a carbonylating reaction to take place by suspending the solid metal. catalyst in a liquid reaction composition containing an organic solvent composed of methanol, methyl iodide, acetic acid and/or methyl acetate and water to a small content ratio and blowing carbon monoxide gas into the liquid reaction composition;

a first separation step of separating and taking out the liquid reaction composition and off gas from the reaction step;

a second separation step of conducting an operation of flash evaporation by introducing the liquid reaction composition separated in the first separation step into a flash vessel and thereby separating a gaseous fraction flowing out from an upper tower section and a liquid fraction flowing out from a lower tower section;

a third separation step of leading the gaseous fraction separated in the second separation step into a distillation system and separating off gas, a product acetic acid fraction, a heavy fraction and a circulating fraction;

a circulation step of returning the liquid fraction separated in the second separation step and the circulating fraction separated in the third separation step to the reactor;

a first absorption step of conducting an operation of gas absorption for the off gas separated in the first separation step, using methanol as absorbent liquid;

a second absorption step of conducting an operation of gas absorption for the off gas separated in the third separation step, using methanol as absorbent liquid under a pressure lower than that of the first absorption step; and an exhaustion step of exhausting the off gas left after the first absorption step, the off gas left after the second absorption step and the heavy fraction separated in the third separation step to the outside of the system; and that methanol that is regulated for temperature to 10 to 25° C. is used as absorbent liquid in the first and second absorption steps and divided so as to use 50 to 80wt % of the entire methanol to be used in the two absorption steps in the second absorption step and the methanol left after the two absorption steps is used as raw material methanol in the reaction step.

BEST MODE FOR CARRYING OUT THE INVENTION

Now, the present invention will be described by referring to the accompanying drawings that illustrate preferred embodiments of the invention.

Figure 1:
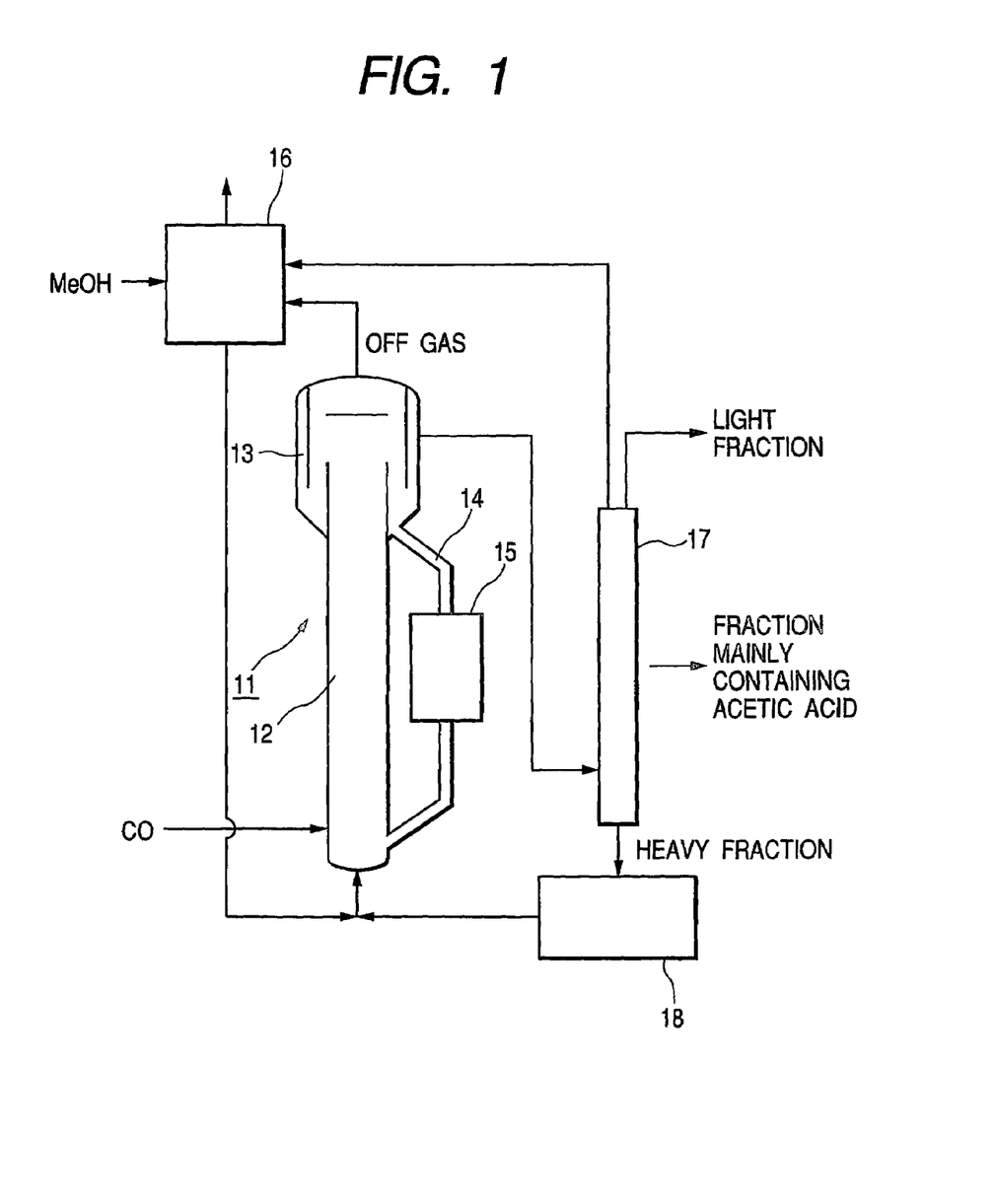
FIG. 1 is a schematic diagram of an exemplar bubble column reactor that can be used for a method of manufacturing acetic acid according to the invention.

FIG. 1 is a schematic diagram of an exemplar bubble column reactor provided with an external circulation system that can be used for a method of manufacturing acetic acid according to the invention. When manufacturing acetic acid, using such a reactor, firstly a solid catalyst is filled into a cylindrical riser section 12 of a reactor 11. The solid catalyst that is generally used for manufacturing acetic acid is one that contains rhodium complex carried on a basic resin having a porous, crosslinked structure. For example, the use of a solid catalyst in which metal rhodium is carried by vinylpyridine resin is particularly preferable. Then, a mixture solution of methanol that is the reaction raw material, a reaction solvent and a promoter is filled into the reactor that is already filled with the solid catalyst. The reaction solvent may be selected from various known solvents. Generally, an organic solvent containing carbonyl groups having two or more carbon atoms is preferably used as reaction solvent. Particularly, the use of acetic acid and methyl acetate is preferable. Generally, an alkyl iodide such as methyl iodide may be used as promoter.

Then, a mixture solution of methanol that is the reaction raw material, a reaction solvent and a promoter is supplied from the bottom of the riser section 12 of the reactor 11 that is already filled with methanol, a solvent and a solid catalyst and, at the same time, CO gas is injected also from the bottom and caused to rise upward. As the injected CO gas rises as bubbles in the liquid contained in the riser section 12, the catalyst is also moved upward in the cylindrical reactor by the gas lift effect. At this time, the partial pressure of carbon monoxide in the reactor is held between 1.0 and 2.5 MPa, preferably between 1.7 and 2.2 MPa, and the exhaustion ratio of carbon monoxide is regulated so as to be between 3 and 15%, preferably between 5 and 10%, of the theoretical reaction volume of carbon monoxide. At this time, the operating conditions are preferably so selected that the gas superficial velocity (the average value of the gas superficial velocity in the gas lead-in section at the bottom of the reactor and the counterpart at the top of the reactor) of carbon monoxide gas is held between 2 and 8 cm/sec. The gas superficial velocity of carbon monoxide gas influences the stable circulation of the catalyst and the Kla value. The liquid circulation velocity can fall below 0.2 m/sec and/or a sufficiently large Kla value may not be obtained to lower the productivity when the gas superficial velocity of carbon monoxide gas is less than 2 cm/sec.

On the other hand, carbon monoxide will be wasted to a large extent and the internal pressure of the reactor will rise to make the reaction poorly economical when the gas superficial velocity of carbon monoxide gas exceeds 8 cm/sec.

The carbonylating reaction of methanol by carbon monoxide progresses to produce acetic acid when the reaction temperature and the total reaction pressure are made to be between 170 and 190° C. and between about 3.0 and 4.5 MPa respectively. At this time, methanol may partly react with methanol and/or produced acetic acid to by turn produce dimethyl ether, methyl acetate, water and so on as byproducts. Note that the rate of reaction falls remarkably to reduce the productivity when the water concentration in the reactor falls below 2 wt %. On the other hand, the energy load of the facility for separating the product of acetic acid from the reaction solution increases and the concentration of corrosive hydrogen iodide also increases when the water concentration in the reactor exceeds 10 wt %. Then, a large facility will be required to consequently reduce the economy of manufacturing acetic acid. Therefore, the water concentration in the reactor is regulated so as to be between 2 and 10 wt %.

By the separator section 13 arranged at an upper part of the reactor 11, the reaction solution containing the solid catalyst that rises in the riser section 12 is then partly taken out from an upper part of the separator section 13 as liquid reaction product that does not contain any solid catalyst, while the remaining reaction solution that contains the solid catalyst returns to the bottom of the reactor through a down-comer section 14 so as to be supplied again to the cylindrical reactor and continuously circulate. The liquid superficial velocity of the reaction solution that rises in the reactor is regulated so as to be found between 0.2 and 1.0 m/sec. With this arrangement, the solid catalyst is dispersed uniformly and a necessary level of circulation/fluidization of the solid catalyst can be maintained on a stable basis. Additionally, it is preferable to arrange a heat exchanger 15 in the down-comer section 14 that operates as external circulation path in order to remove the generated heat because the carbonylating reaction of methanol is an exothermic reaction. Excessively supplied CO gas is drawn out from the top of the separator section 13 as off gas and fed to an exhaust gas absorption device 16, where it is washed by the liquid reaction raw material to be supplied to the reactor.

The liquid reaction product separated by the separator 13 is then fed to flash column 17, where the light fraction containing mainly methyl iodide, methyl acetate and water, the fraction containing mainly acetic acid and the heavy fraction containing the rhodium catalyst, acetic acid, methyl acetate, methyl iodide, water and methanol are taken out respectively from the top section, the middle section and the bottom section of the flash column 17 so as to be separated from each other. Of the drawn out fractions, heavy components are returned to the reactor for circulation. However, heavy components include nitrogen-containing compounds such as pyridine compounds that are produced as decomposition products of the vinylpyridine resin and released from the latter to a small extent and, if such compounds are accumulated in the circulating liquid, they induce release of rhodium complex ions to consequently reduce the effectiveness of the catalyst. Therefore, it is preferable to process at least part of the heavy components by means of a nitrogen-containing compounds removing device 18 to eliminate any nitrogen-containing compounds that can induce release of rhodium complex ions. A device filled with ion-exchange resin may suitably be used for such a nitrogen-containing compounds removing device 18. The gaseous components (mainly CO gas) dissolved in the light fraction are absorbed by the methanol that is fed to the exhaust gas absorption device and supplied to the reactor.

Figure 2:
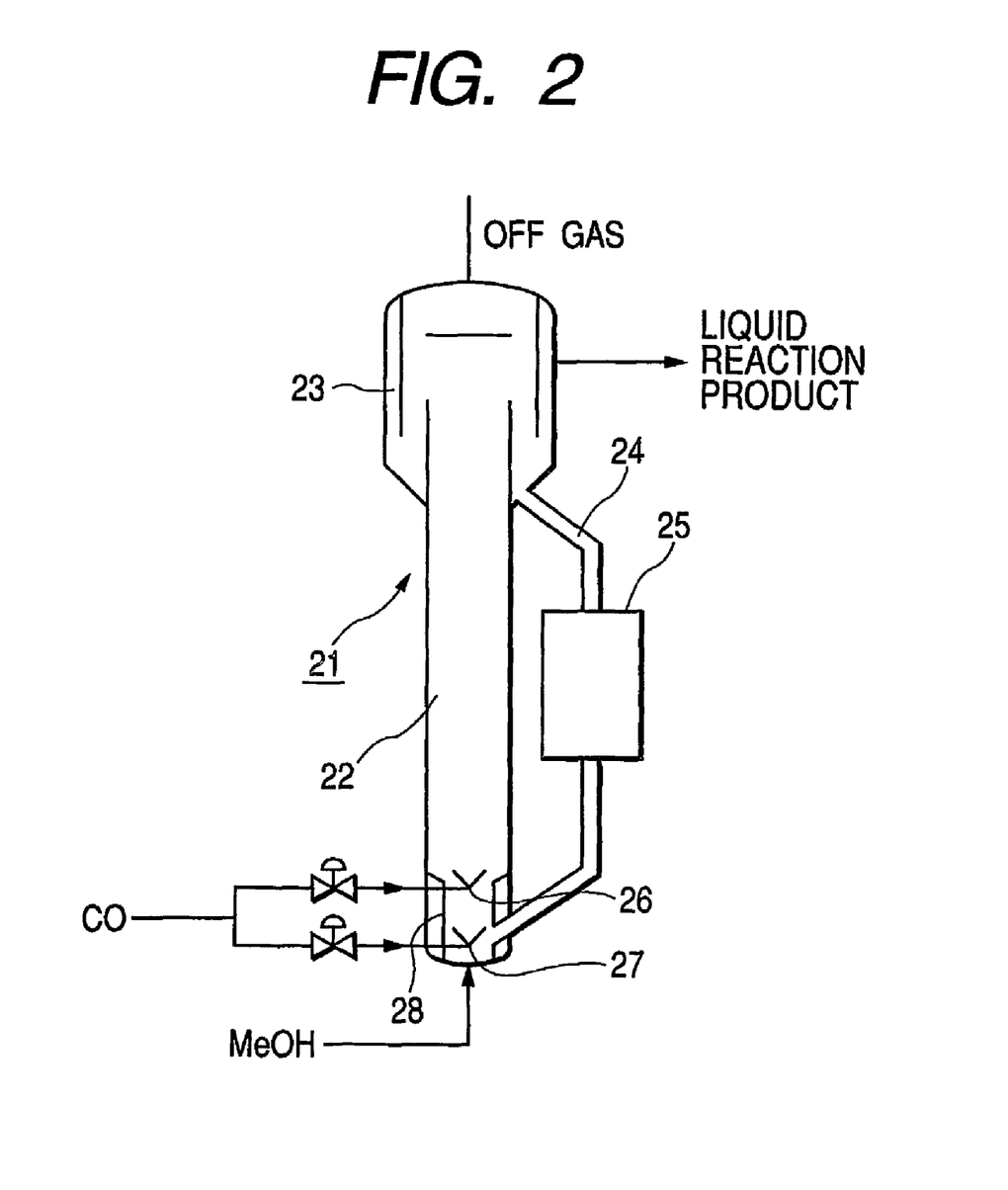
FIG. 2 is a schematic diagram of another exemplar bubble column reactor that can be used for a method of manufacturing acetic acid according to the invention.

FIG. 2 is a schematic diagram of another exemplar bubble column reactor also provided with an external circulation system that can be used for a method of manufacturing acetic acid according to the invention. A reactor 21 has a cylindrical reaction section (riser section 22) where a reaction solution containing carbon monoxide gas and a solid catalyst rises and provided in the bottom zone thereof with a narrowed section 28 whose inner diameter is 30 to 70% of that of the riser section 22. A separator section 23 is arranged at the top of the riser section 22 and adapted to collect carbon monoxide gas that remains without reacting from the reaction solution that contains the carbon monoxide gas and the solid catalyst and at the same time separate the liquid reaction product that does not contain the solid catalyst and the reaction solution that contains the remaining solid catalyst. A liquid down-flow zone (down-comer section 24) for circulating the separated reaction solution that contains the remaining solid catalyst is connected at an end thereof to the bottom of the separator section 23 and at the opposite end to a bottom part of the reactor 21 for the purpose of supplying the reaction liquid again to cylindrical reaction section. A heat exchanger 25 is arranged at a middle part of the down-comer section 24 for the purpose of eliminating the heat generated in the carbonylating reaction of methanol that is an exothermic reaction. The ratio of the length L to the diameter D, or L/D, of the reactor is preferably not smaller than 8 because it is necessary to provide a sufficiently long gas/liquid contact time and a sufficient level of circulation/fluidization for achieving a satisfactorily high reaction efficiency.

First carbon monoxide blow-in port 26 and second carbon monoxide blow-in port 27 are provided as a carbon monoxide blow-in port so as to take the role of fluidizing the solid catalyst in the reactor and that of mobilizing the solid catalyst in a lower part of the reactor respectively. Each of the blow-in ports may take the form of a single pipe nozzle having a gas injection hole at the front end of the pipe, that of a nozzle of a ring-shaped or branched pipe having a large number of gas injection holes arranged at the peripheral wall of the pipe or some other form. While it is preferable to arrange at least a carbon monoxide blow-in port for fluidizing the solid catalyst and at least a carbon monoxide blow-in port for mobilizing the solid catalyst at respective levels, a plurality of blow-in ports may be arranged for fluidizing the solid catalyst and/or for mobilizing the solid catalyst whenever necessary.

In the reactor of FIG. 2, the second carbon monoxide blow-in port 27 for mobilizing the solid catalyst is arranged near the junction of the narrowed section 28, which is located at a lower part of the reactor where the solid catalyst is apt to be deposited to clog the circulation path, and the external circulation path, the junction (circulation lead-in section) being located near the lower end of the narrowed section 28. On the other hand, the first carbon monoxide blow-in port 26 for fluidizing the solid catalyst is arranged at an upper part of the narrowed section 28 above the second carbon monoxide blow-in port 27. The appropriate position of the first carbon monoxide blow-in port 26 can be selected as a function of the profile of the reactor 21, the concentration of the solid catalyst, the operating conditions of the reactor and other factors.

When manufacturing acetic acid, using a bubble column reactor with an external circulation system as shown in FIG. 2, firstly a solid catalyst is filled into the cylindrical riser section 22 of the reactor 21. The solid catalyst that is generally used for manufacturing acetic acid is one that contains rhodium complex carried on a basic resin having a porous, crosslinked structure. For example, the use of a solid catalyst in which metal rhodium is carried by vinylpyridine resin is particularly preferable. The catalyst rhodium is contained normally 0.3 to 2.0 wt % of the basic resin. Then, a mixture solution of methanol that is the reaction raw material, a reaction solvent and a promoter is filled into the reactor that is already filled with the solid catalyst. The reaction solvent may be selected from various known solvents. Generally, an organic solvent containing carbonyl groups having two or more carbon atoms is preferably used as reaction solvent. Particularly, the use of acetic acid and methyl acetate is preferable. Generally, an alkyl iodide such as methyl iodide may be used as promoter.

Then, a mixture solution of methanol that is the reaction raw material, a reaction solvent and a promoter is supplied from the bottom of the riser section 22 of the reactor 21 that is filled with methanol, a solvent and a solid catalyst and, at the same time, CO gas is injected through the first carbon monoxide blow-in port 26 and the second carbon monoxide blow-in port 27. The CO gas injected through these carbon monoxide blow-in ports rises as bubbles in the liquid contained in the riser section 22, the catalyst is also moved upward in the cylindrical reactor by the gas lift effect.

Of the reaction solution containing CO gas and the solid catalyst that rises in the riser section 22, the unreacted CO gas is collected as off gas, while the liquid reaction product that does not contain the solid catalyst is separated from the remaining reaction solution that contains the solid catalyst in the separator section 23 arranged at the top of the reactor 21. The liquid reaction product that does not contain the solid catalyst is then fed further to the acetic acid refining step, while the reaction solution that contains the solid catalyst returns to the bottom of the reactor by way of the down-comer section 24 so as to be fed to the cylindrical reactor once again for circulation. At this time, any excessive heat generated by the carbonylating reaction of methanol, which is an exothermic reaction, is removed by a heat exchanger 25 that is arranged at a middle part of the down-comer section 24 of the external circulation path.

In this embodiment of bubble column reactor, the first carbon monoxide blow-in port 26 arranged at an upper part of the narrowed section 28 mainly takes the role of fluidizing the solid catalyst, whereas the second carbon monoxide blow-in port 27 arranged near the junction of the bottom of the narrowed section 28 and the external circulation path mainly takes the role of mobilizing the solid catalyst at a lower part of the reactor, where the solid catalyst is apt to be deposited to clog the circulation path, and loosening and fluidizing the solid catalyst in the down-comer section. While the flow rate of CO gas led to each of the carbon monoxide blow-in ports can be appropriately regulated within a range that allows to conduct the operation of reaction on a stable basis depending on the concentration of the solid catalyst, the operating conditions and the like, the ratio of the flow rate of CO gas led to the carbon monoxide blow-in port for fluidizing the solid catalyst to the flow rate of CO gas led to the carbon monoxide blow-in port for mobilizing the solid catalyst is preferably found within a range between 70:30 and 90:10.

With regard to the operating conditions of the bubble column reactor, the carbonylating reaction of methanol by carbon monoxide progresses to produce acetic acid when the reaction temperature, the total reaction pressure and the partial pressure of carbon monoxide are made to be between 170 and 190° C., between 1.5 and 6.0 MPa and between about 1.0 and 2.5 MPa respectively. At this time, methanol may partly react with methanol and/or produced acetic acid to by turn produce dimethyl ether, methyl acetate, water and so on as byproducts.

Figure 3:
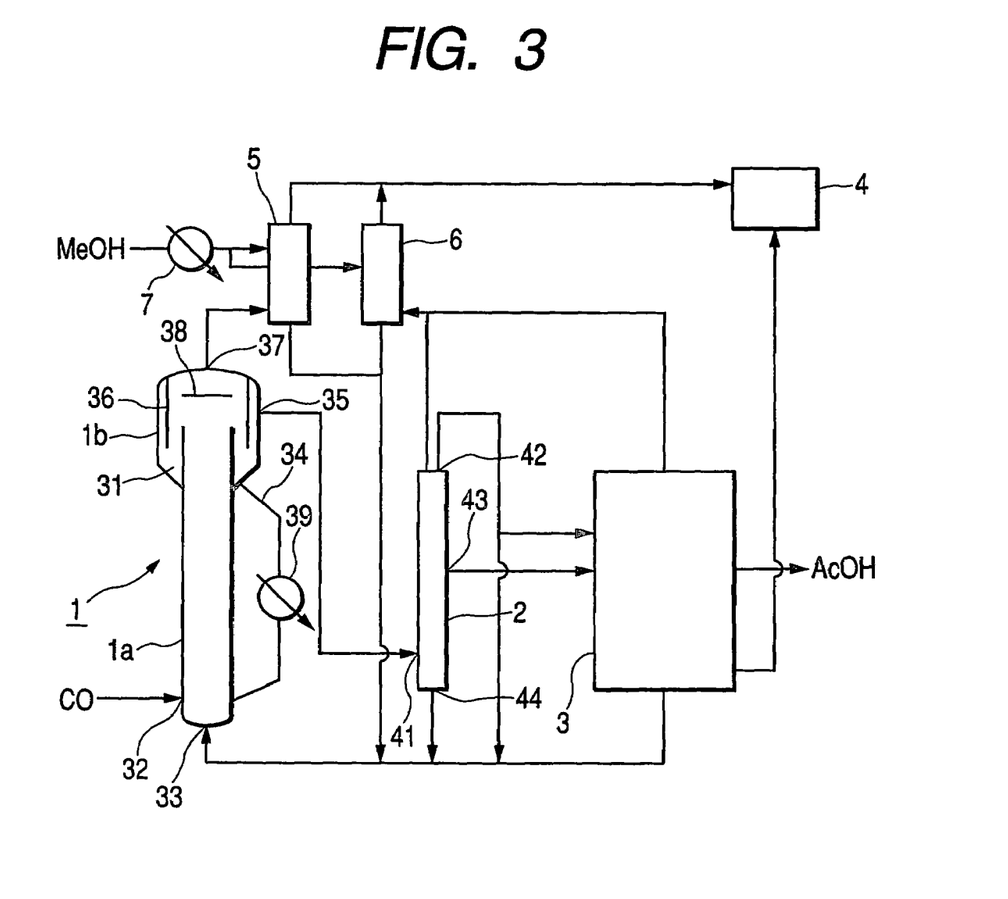
FIG. 3 is a schematic diagram of another embodiment of method of manufacturing acetic acid according to the invention.

FIG. 3 is a schematic diagram of another embodiment of method of manufacturing acetic acid according to the invention. Referring to FIG. 3, the reactor 1 comprises an upright cylindrical riser 1a having a closed bottom and an open top and a separator 1b having a diameter greater than the diameter of the riser 1a and fitted to the top of the riser 1a. The lower end of the separator is tightly held in contact with the outer wall surface of the riser at an upper part of the latter to produce a closed internal space in the reactor and define a ring-shaped pocket section 31 between the outer wall surface of an upper part of the riser and the inner wall surface of a lower part of the separator. In the riser, a solid/liquid mixture is formed as particles of a rhodium-containing solid catalyst are suspended in a liquid reaction composition containing methanol that is one of the reaction raw materials, methyl iodide that is a promotor, an organic solvent of acetic acid and/or methyl acetate and water that shows only a small content ratio (2 to 10 wt %). Then, a bubble column gas/liquid contact operation is conducted as carbon monoxide gas is blown into the solid/liquid mixture from the bottom of the riser. Thus, the operation of synthetically producing acetic acid by carbonylation of methanol proceeds in the reactor when the reaction temperature and the reaction pressure are made to be between 170 and 190° C. and between 3.5 and 4.5 MPa respectively. The riser is provided at the bottom thereof with a liquid inlet port 33 for introducing the liquid reaction composition in addition to a gas inlet port 32 for blowing in carbon monoxide gas so that the liquid reaction composition is introduced continuously to form a rising flow of the solid/liquid mixture in the riser. Then, as a result, a rising flow of a mixture that shows three phases of gas/liquid/solid is formed to produce acetic acid as bubbles of carbon monoxide gas are made to rise in the former rising flow and become combined with the former rising flow. When the rising flow in the riser that shows three phases gets to the separator, particles of the solid catalyst and bubbles of carbon monoxide gas are separated from the liquid reaction composition. This will be described in greater detail below. Of the rising flow in the riser that shows three phases of gas/liquid/solid, the particles of the solid catalyst spill out from the top end of the riser and circulate back to the bottom of the riser by way of the pocket section 31 and the external circulation path 34. On the other hand, of the liquid reaction composition and the bubbles separated from the particles of the solid catalyst at the top of the riser, the liquid reaction composition flows out through liquid outlet port 35 arranged at an upper part of the lateral wall of the separator. A partition plate 36 having a diameter greater than the diameter of the riser and smaller than that of the separator is arranged in the separator to prevent particles of the solid catalyst separated from the liquid reaction composition from being discharged through the outlet port of the liquid product. Since the liquid reaction composition forms a free surface in the separator, bubbles contained in the liquid reaction composition are separated from the latter to form a region of gas phase above the free surface and eventually discharged through gas outlet port 37 arranged at the top of the separator (first separation step). Additionally, a baffle plate 38 is arranged vis-à-vis the open top end of the riser in the separator so as to prevent droplets of the liquid reaction composition from being discharged through the gas outlet port to accompany the bubbles separated from the liquid reaction composition and expelled through the gas outlet port. A cooler 39 is arranged at a middle part of the external circulation path 34 in order to remove heat generated by the reaction and maintain the internal temperature of the reactor to a constant level.

The liquid reaction composition that flows out through the liquid outlet port 35 of the reactor is led into a flash column 2, the internal pressure of which is substantially held to the atmospheric pressure level, through lower inlet port 41 of the flash column and divided into off gas and a light liquid fraction that flow out through tower top outlet port 42, a crude acetic acid fraction that flows out through tower middle outlet port 43 and a circulating fraction that flows out through tower bottom outlet port 44 (second separation step). The off gas contains carbon monoxide that has been dissolved in the liquid reaction composition and gasified methyl iodide, while the light liquid fraction mainly contains methyl acetate, acetic acid and water. If necessary, excessive water is separated from the light liquid fraction by means of an oil/water separator (not shown). Subsequently, part of the light liquid fraction is fed to a downstream distillation system 3, while the remaining part of the light liquid fraction is returned to the reactor 1. While the crude acetic acid fraction contains water, methyl iodide, propionic acid and other reaction byproducts in addition to acetic acid, all of them are basically totally fed to the downstream distillation system 3. The circulating fraction contains nitrogen compounds, rhodium complex and so on that are separated from particles of the solid catalyst in addition to acetic acid, methyl acetate, methyl iodide, water, and methanol which are returned to the reactor 1, although part of the circulating fraction may have to be bypassed through a nitrogen removing column (not shown) in order to remove the nitrogen compounds. The remaining part of the liquid light fraction and the crude acetic acid fraction fed to the distillation system 3 are divided into off gas, a product acetic acid fraction, a heavy fraction that is to be incinerated by an incinerator 4 (and contains propionic acid and other reaction byproducts) and a circulating fraction (mainly containing acetic acid, water and methanol) that is returned to the reactor 1 (third separation step).

Off gas is discharged from the reactor 1, the flash column 2 and the distillation system 3. Since such off gas contains gasified methyl iodide and an organic solvent in addition to unreacted carbon monoxide, the useful substances are collected by absorption towers 5 and 6 and the remaining substances are incinerated in the incinerator 4. Since the off gas coming out of the reactor 1 is pressurized, it is treated in the high-pressure absorption tower 5 the inside of which is pressurized to 3 to 5 MPa (first absorption step). On the other hand, the off gas coming out of the flash column 2 and the distillation system 3 substantially shows atmospheric pressure so that it is treated in the low-pressure (atmospheric pressure) absorption tower 6 (second absorption step). By using a high-pressure absorption tower and a low-pressure absorption tower in parallel, all raw material methanol can be used effectively as absorber for absorbing useful substances contained in off gas. While the off gas that is treated in the high-pressure absorption tower may be treated further in the low-pressure absorption tower 6, the collection effect and the installation cost may need to be considered when such an arrangement is employed.

Figure 4:
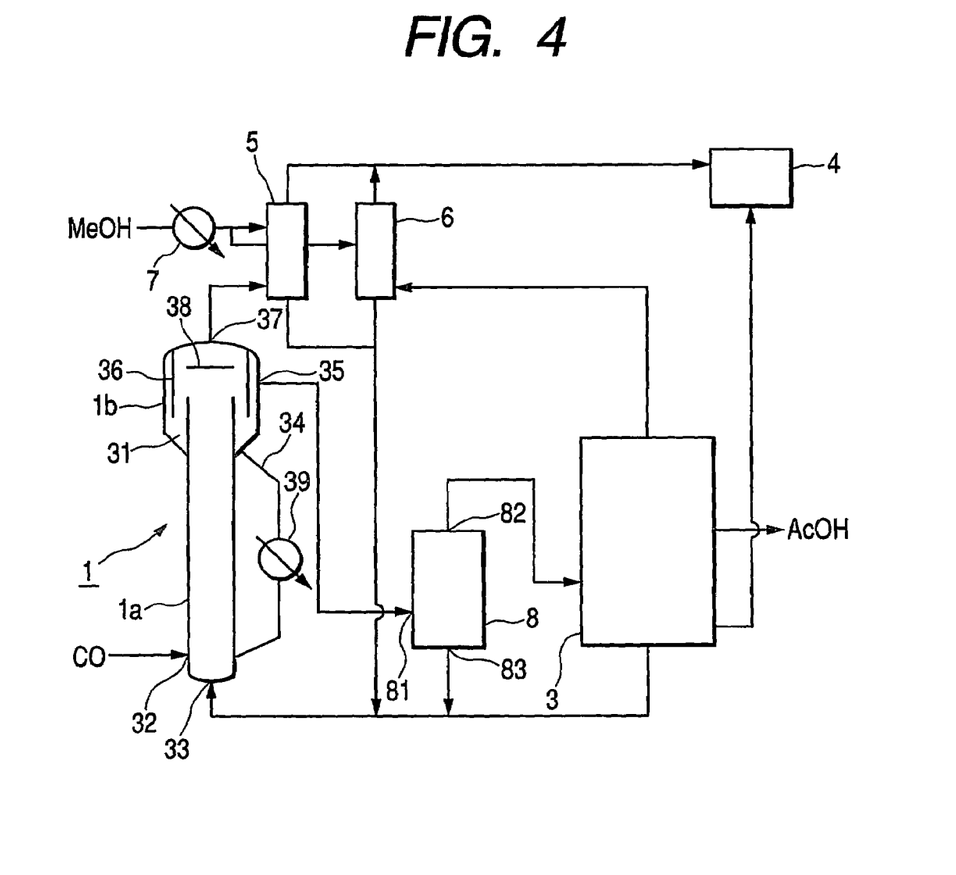
FIG. 4 is a schematic diagram of still another embodiment of method of manufacturing acetic acid according to the invention.

FIG. 4 is a schematic diagram of still another embodiment of method of manufacturing acetic acid according to the invention. The arrangement of FIG. 4 differs from that of FIG. 3 in that the liquid reaction composition flowing out of the reactor 1 is led into flash vessel 8 through an inlet port 81, where flash evaporation takes place instead of flash distillation. More specifically, the liquid reaction composition is evaporated in the flash vessel under reduced pressure and divided into a gaseous fraction and a liquid fraction of the remaining liquid (second separation step). The gaseous fraction contains carbon monoxide that has not reacted but has been dissolved in the liquid reaction composition and methyl iodide as well as crude acetic acid that is to be refined to product acetic acid in a subsequent distillation step and part of the organic solvent and the byproducts, all of which flow out through an upper outlet port 82 of the flash vessel and led into the distillation system 3. Therefore no off gas is discharged from the flash vessel 8. On the other hand, the liquid fraction contains the organic solvent, heavy substances and nitrogen compounds that flows out from particles of the solid catalyst, which flow out through lower outlet port 83 of the flash vessel and return to the reactor 1. Otherwise, the arrangement of FIG. 4 is the same as that of FIG. 3.

Raw material methanol is used as absorbent liquid in the absorption towers 5 and 6. The use of raw material methanol makes the conventional diffusion step unnecessary and the methanol that has been used as absorbent liquid can be led into the reaction tower without processing it. The temperature of methanol that is used in the absorption towers 5 and 6 is regulated to 10 to 25° C. (normally cooled by cooler 7) in order to improve the efficiency of absorbing useful substances contained in off gas. The absorption efficiency is low when the methanol temperature exceeds 25° C. For example, when absorbing and removing methyl iodide from off gas, the ratio of loss generally goes above 0.1% when the methanol temperature exceeds 25° C. On the other hand, when the methanol temperature is lower than 10° C., the temperature of the coolant also needs to be lowered to uneconomically raise the operating cost.

Methanol that is used as absorbent liquid is distributed to the high-pressure absorption tower 5 and the low-pressure absorption tower 6. The loss of methyl iodide and methanol that flows out of the system can advantageously be minimized when 50 to 80%, preferably 55 to 70%, of all of the methanol that flows through the absorption towers is distributed to the low-pressure tower (low-pressure tower distribution ratio). Since the ratio of the flow rate of off gas from the reactor 1 to that of off gas from the flash column 2 and the distillation system 3 is approximately between 1.5:1 and 1:1.5, the ratio of the flow rate of absorbent liquid to that of off gas is between 1/1.0 and 1/0.25 in the high-pressure absorption tower and between 1/0.2 and 1/0.4 in the low-pressure absorption tower.

In the case of carbonylation of methanol by means of a heterogeneous catalyst reaction conducted in a reactor 1, while both acetic acid that is the reaction product and/or methyl acetate that is a byproduct of the reaction are used as solvent, the solubility of the catalyst, which is rhodium complex, does not give rise to any problem unlike the case of a homogenous catalyst reaction. In other words, water does not need to be present to a large extent. Normally, water is required to exist only by 2 to 10 wt %. On the other hand, rhodium complex carried by insoluble resin particles that contains a pyridine ring in the molecular structure is used as solid metal catalyst. More specifically, a catalyst in which rhodium carbonyl complex $[Rh(CO)_2I_2]^-$ is carried, by ion exchange, by pyridine resin whose pyridine part is turned to be quaternary by alkyl iodide is suitably be used. However, when the acetic acid manufacturing operation is conducted for a prolonged period of time, there may arise a problem that the pyridine skeleton of pyridine resin that is turned to be quaternary can be partly released from the resin and dissolved into the liquid phase. Then, the rhodium carbonyl complex can accompany the pyridine skeleton (nitrogen compound) that is released from the resin and become contained in the liquid reaction composition. The rhodium carbonyl complex that comes to be contained in the liquid reaction composition is deposited in the flash column (or flash vessel) as a result of reduced pressure and condensation. Therefore, the circulating fraction from the flash column that is recycled to the reactor is preferably partly bypassed to a nitrogen removing column in order to avoid accumulation of nitrogen compounds in the liquid reaction composition.

As for the type of the reactor, the bubble column reactor as shown in FIGS. 3 and 4 is preferable. A conventional agitation tank type reactor is accompanied by a problem that resin particles that operate as carriers of the solid metal catalyst can easily be crushed. Further, it is not easy to separate particles of the solid catalyst from the liquid reaction composition unlike the bubble column reactor. From this point of view, in the case of a bubble column reactor, particles of the solid catalyst can be separated with ease from the liquid reaction composition if liquid is drawn from above the layer of catalyst particles (which is expanded due to a rising flow in the reactor) because the particles of the solid catalyst are less subjected to mechanical impacts and hence resin particles can hardly be crushed. With a bubble column reactor shown in FIG. 3 that is adapted to circulate particles of the solid catalyst, the resin layer rises above the top of the riser so that, while the top surface of the resin layer is not formed in the riser, particles of the solid catalyst spill from the top of the riser without rising further and hence the top surface of the resin layer is produced there because the diameter of the reactor is suddenly increased in the separator to reduce the flow rate of the rising liquid flow. As a result, particles of the solid catalyst are separated from the liquid reaction composition.

In a bubble column reactor, the concentration of suspended particles of the solid catalyst needs to be held lower than its counterpart of an agitation tank type reactor in order to uniformly disperse particles of the solid catalyst into the liquid reaction composition. Therefore, it has disadvantages, for example, a rate of reaction is limited. However, with a bubble column reactor as shown in FIG. 3 that is adapted to circulate particles of the solid catalyst, particles of the solid catalyst are forced to circulate from the top to the bottom of the tower by way of an external circulation path so that the particles of the solid catalyst can highly efficiently contact with the liquid reaction composition even when the concentration of suspended particles of the solid catalyst is raised. Since carbon monoxide gas is blown into the riser, there consequently arises an internal density difference between the inside of the riser and the external circulation path so that a flow of circulating particles of the solid catalyst takes place without effort. The circulation will be highly smooth when the profile and the position of the carbon monoxide blow-in port and those of the liquid reaction composition blow-in port are appropriately designed so as to encourage the movement of particles of the solid catalyst on the bottom of the riser.

Now, the present invention will be described further by way of examples.

EXAMPLES 1, 2 AND COMPARATIVE EXAMPLE 1 THROUGH 3

In each example, acetic acid was manufactured experimentally by using an experimental bubble column reactor with an external circulation system as shown in FIG. 1 (height 15 m, inner diameter of reactor 150 mm). After filling a predetermined amount of catalyst (vinylpyridine type ion exchange resin carrying rhodium complex by 0.85 wt % of rhodium per resin, specific gravity 1.2, average particle diameter 0.45 mm) into the reactor, acetic acid was filled into the riser section 12 by way of liquid lead-in pipe. Subsequently, CO was injected so as to make it flow upward from the bottom of the riser section 12 at a predetermined flow rate in order to cause acetic acid and the catalyst to start circulating and, at the same time, part of the acetic acid that spilled due to the introduced CO was drawn out from the separator section 13 by way of piping. Excessive CO gas was exhausted from the top of the separator section 13. The internal pressure of the reactor was held to a predetermined pressure level by means of valve regulation and the internal temperature of the cylindrical reactor was raised to a predetermined temperature level by means of a heater while acetic acid and the solid catalyst were being forced to circulate. Thereafter, the reaction raw material was introduced into the reactor by way of piping at a constant rate and the spilled reaction liquid was drawn out from the separator section 13 by way of piping.

An experiment was conducted in each of the examples by following the above described operation procedure under the conditions listed in Table 1. The Kla values were observed and the overall reaction productivities (acetic acid producing rate per unit reaction volume, kmol/h/m$^3$) achieved by the experiments were compared. The productivity of Example 1 was used as reference value (mark 10) and the achievements of the examples were rated on a relative basis. Table 1 also shows the obtained results.

TABLE 1

| | Concentration of solid catalyst (kg/m$^3$) | CO partial pressure (MPa) | CO discharge ratio (%) | Liquid superficial velocity (m/sec) | Kla value (1/Hr) | Overall reaction productivity (acetic acid kmol/h)/m$^3$ |
|---|---|---|---|---|---|---|
| Example 1 | 280 | 1.8 | 7 | 0.30 | 1000-5000 | 10 |
| Example 2 | 280 | 1.8 | 15 | 0.40 | 1500-5500 | 12 |
| Comp Ex. 1 | 280 | 1.8 | 2 | 0.25 | 300-4500 | 7 |
| Comp Ex. 2 | 280 | 0.9 | 5 | 0.20 | 500-4500 | 3 |
| Comp Ex. 3 | 90 | 1.8 | 5 | 0.15 | 500-4500 | 3 |

EXAMPLE 3

Acetic acid was manufactured experimentally by using an experimental bubble column reactor with an external circulation system as shown in FIG. 2 (height 6 m, inner diameter of riser section 125 mm, diameter of narrowed section 75 mm). A predetermined amount of catalyst (vinylpyridine type ion exchange resin carrying rhodium complex, specific gravity 1.2, average particle diameter 0.45 mm) was filled into the reactor 21 so as to make the concentration of the solid catalyst per reaction volume to be equal to 135 kg/m$^3$. Then, acetic acid was filled into the riser section 22 by way of liquid lead-in pipe and subsequently carbon monoxide (CO) was injected through the carbon monoxide blow-in ports so as to make it flow upward as jet stream at a predetermined flow rate in order to cause acetic acid and the catalyst to start circulating. At this time, part of the acetic acid that spilled due to the introduced CO was drawn out from the separator section 23 by way of piping. Excessive CO gas was exhausted from the top of the separator section 23. The internal pressure of the reactor was held to a predetermined pressure level by means of valve regulation and the internal temperature of the cylindrical reactor was raised to a predetermined temperature level by means of a heater while acetic acid and the solid catalyst were being forced to circulate. Thereafter, the reaction raw material was introduced into the reactor by way of piping at a constant rate and the spilled reaction liquid was drawn out from the separator section 23 by way of piping.

The carbon monoxide blow-in port of the first level was arranged at an upper part of the narrowed section and the second carbon monoxide blow-in port of the second level was arranged below the first level carbon monoxide blow-in port and near the junction of the narrowed section and the circulation line located at the bottom of the narrowed section. A branched pipe gas distributor was used for the blow-in ports. CO gas was introduced at a flow rate of 340 NL/min from the first step carbon monoxide blow-in port and at a flow rate of 86 NL/min from the second step carbon monoxide blow-in port. The reaction proceeded on a stable basis while manufacturing acetic acid under the above described conditions.

COMPARATIVE EXAMPLE 4

Acetic acid was manufactured as in Example 3 except that only a single carbon monoxide blow-in port of a branched pipe gas distributor was arranged at an upper part of the narrowed section and CO gas was introduced at a flow rate of 340 NL/min. As a result, the volume of the circulating material was gradually reduced as a result of deposition of the solid catalyst and hence the reaction did not proceed on a stable basis. At the same time, gas stayed on the bottom of the solid and in the down-comer section as a result of short pass so that it took long time before a circulating flow was produced.

EXAMPLE 4

Acetic acid was synthetically manufactured by carbonylation of methanol, using the process flow illustrated in FIG. 3. Acetic acid and methyl iodide were put into the reactor 1 respectively by 10 kg and 2 kg and pyridine resin that was turned to be quaternary and rhodium carbonyl complex [Rh(CO)$_2$I$_2$]$^-$ were added thereto to prepare a rhodium-containing solid catalyst in the reactor. Subsequently, methanol was introduced through the liquid inlet port 33 by way of the absorption towers 5 and 6 at a rate of 5.3 kg/min, while carbon monoxide was introduced through the gas inlet port 32 at a rate of 4.2 L/min. The liquid reaction composition that flowed out from the reactor 1 was continuously refined in the flash column 2 and the distillation tower 3 to obtain product acetic acid and the circulating fraction that flowed out from the two towers was returned to the liquid inlet port of the reactor 1. Table 2 shows the operating conditions of the reactor 1, the flash column 2 and the distillation tower 3. The off gas from the reactor 1 was made to pass through the high-pressure absorption tower 5 while the off gas from the flash column 2 and the distillation tower 3 was made to pass through the low-pressure absorption tower 6 before they were incinerated with the heavy fraction from the distillation tower 3 in the incinerator 4. After the operation reached a stable state, the temperature of the methanol that was used as absorbent liquid and the distribution ratio of the low-pressure absorption tower were modified. Then, the ratio of collected methyl iodide and the loss of methanol and carbon monoxide were observed by measuring the flow rate using a flow meter and conducting a composition analysis using a gas chromatography. The obtained results are listed in Table 3.

TABLE 2

| | Temperature ° C. | Pressure MPa | Flow rate kg/h |
|---|---|---|---|
| Reactor | | | |
| inside | 180 | 4.0 | |
| off gas | | | 0.78 |
| Flash column | | | |
| tower bottom | 141 | 0.27 | |
| receiver | 46 | 0.20 | |
| off gas | | | 0.75 |
| Distillation tower | | | |
| tower bottom | 148 | 0.24 | |
| receiver | 50 | 0.24 | |
| off gas | | | 0.01 |

TABLE 3

| | | | Flow out ratio (%) | | |
|---|---|---|---|---|---|
| Absorbent Liquid | Temp. ° C. | Distribution ratio | CH$_3$I | Absorbent liquid | CO |
| Methanol | 20 | 60 | 0.07 | 0.5 | 90 |
| Methanol | 20 | 50 | 0.50 | 0.6 | 90 |
| Methanol | 20 | 80 | 0.10 | 0.5 | 91 |
| Methanol | 20 | 40 | 1.50 | 0.7 | 90 |
| Methanol | 20 | 90 | 1.00 | 0.7 | 92 |
| Methanol | 25 | 60 | 0.08 | 0.5 | 90 |
| Methanol | 10 | 60 | 0.06 | 0.5 | 90 |
| Methanol | 40 | 60 | 0.30 | 0.6 | 91 |
| Acetic acid | 25 | 60 | 0.05 | 0.2 | 92 |

The invention claimed is:

1. A method of manufacturing acetic acid by carbonylating methanol with carbon monoxide by way of a heterogeneous catalytic reaction in a bubble column reactor, characterized in that the carbonylating reaction is conducted with a solid catalyst concentration of not less than 100 kg/m$^3$ in terms of the reaction volume, wherein the partial pressure of carbon monoxide in the reactor is between 1.0 and 2.5 MPa and the exhaustion ratio of carbon monoxide is between 3 and 15% of the theoretical reaction volume of carbon monoxide, while the liquid superficial velocity is between 0.2 and 1.0 m/sec.

2. A method according to claim 1, wherein the partial pressure of carbon monoxide in the reactor is held within a range between 1.7 and 2.2 MPa.

3. A method according to claim 1, wherein the exhaustion ratio of carbon monoxide is between 5 and 10% of the theoretical reaction volume.

4. A method according to any one of claims 1, 2 or 3, wherein the solid catalyst is formed by causing a vinylpyridine resin carrier to carry rhodium complex.

5. A method according to claim 4, wherein methyl iodide is used as promoter.

6. A method according to any one of claims 1, 2 or 3, wherein acetic acid and methyl acetate are used as solvent.

7. A method according to any one of claims 1, 2 or 3, wherein the water concentration in the reactor is between 2 and 10 wt %.

8. A method according to any one of claims 1, 2 or 3, wherein the ratio of the length L to the diameter D of the bubble column reactor, or L/D, is not smaller than 8.

9. A method according to any one of claims 1, 2 or 3, wherein the bubble column reactor has an external circulation path and a heat exchanger is incorporated in the circulation path.

10. A method according to any one of claims 1, 2 or 3, wherein a liquid reaction product is taken out from the reaction liquid containing the solid catalyst by means of a separator arranged at a top of the reactor and fed to a flash column and a light fraction, a fraction mainly containing acetic acid and a heavy fraction are taken out respectively from a top section, a middle section and a bottom section of the flash column and separated from each other.

11. A method according to claim 10, wherein at least part of the heavy fraction is treated by means of a nitrogen-containing compounds removing device and caused to circulate back to the bubble column reactor.

12. A method according to claim 1, wherein carbon monoxide is injected into the reactor by way of carbon monoxide blow-in ports arranged at a plurality of levels.

13. A method according to claim 12, wherein said plurality of levels are two levels.

14. A method according to claim 12, wherein said bubble column reactor has an external circulation path and said carbon monoxide blow-in ports arranged at a plurality of levels include at least a carbon monoxide blow-in port arranged at a level to fluidize the solid catalyst in the reactor and a carbon monoxide blow-in port arranged at another level to mobilize the solid catalyst in a lower part of the reactor and draw or fluidize the solid catalyst in the external circulation path.

15. A method according to claim 14, wherein the bubble column reactor has a narrowed section at a lower part of the cylindrical reactor with an inner diameter as small as 30 to 70% of the remaining part of the cylindrical reactor and a carbon monoxide blow-in port is arranged at an upper part of the narrowed section to fluidize the solid catalyst while another carbon monoxide blow-in port is arranged near the junction of the reactor and the external circulation path (circulation lead-in section) located at a bottom of the narrowed section to mobilize the solid catalyst and draw or fluidize the solid catalyst in the external circulation path.

16. A method according to any one of claims 12 through 15, wherein the carbon monoxide blow-in ports are branched pipe gas distributors.

17. A method according to any one of claims 12 through 15, wherein a separator is arranged at a top of the reactor in order to collect unreacted carbon monoxide gas from the reaction liquid containing unreacted carbon monoxide gas and the solid catalyst and take out a liquid reaction product not containing the solid catalyst.

18. A method of manufacturing acetic acid by carbonylating methanol with carbon monoxide in the presence of a solid metal catalyst, characterized in that it comprises:

a reaction step of causing a carbonylating reaction to take place in a pressurized bubble column reactor by suspending the solid metal catalyst in a liquid reaction composition containing an organic solvent composed of methanol, methyl iodide, acetic acid and/or methyl acetate and water to a small content ratio and blowing carbon monoxide gas into the liquid reaction composition with a solid catalyst concentration of not less than 100 kg/m$^3$ in terms of the reaction volume;

a first separation step of separating and taking out the liquid reaction composition and off gas from said reaction step;

a second separation step of conducting an operation of flash distillation by introducing the liquid reaction composition separated in the first separation step into a flash column and thereby separating off gas and a light liquid fraction flowing out from a tower top section, a crude acetic acid fraction flowing out from a tower middle section and a circulating fraction flowing out from a tower bottom section;

a third separation step of introducing part of the light liquid fraction and the crude acetic acid fraction separated in said second separation step into a distillation system and thereby separating off gas, a product acetic acid fraction, a heavy fraction and a circulating fraction;

a circulation step of returning the residue of the separated light liquid fraction and the circulating fraction separated in said second separation step and the circulating fraction separated in said third separation step to the reactor;

a first absorption step of conducting an operation of gas absorption for the off gas separated in said first separation step, using methanol as absorbent liquid;

a second absorption step of conducting an operation of gas absorption for the off gas separated in said second separation step and the off gas separated in said third separation step, using methanol as absorbent liquid under a pressure lower than that of said first absorption step; and an exhaustion step of exhausting the off gas left after said first absorption step, the off gas left after said second absorption step and the heavy fraction separated in said third separation step to the outside of the system; and that methanol that is regulated for temperature to 10 to 25° C. is used as absorbent liquid in said first and second absorption steps and divided so as to use 50 to 80 wt % of the entire methanol to be used in the two absorption steps in said second absorption step and the methanol left after the two absorption steps is used as raw material methanol in the reaction step.

19. A method of manufacturing acetic acid by carbonylating methanol with carbon monoxide in the presence of a solid metal catalyst, characterized in that it comprises:

a reaction step of causing a carbonylating reaction to take place in a pressurized bubble column reactor by suspending the solid metal catalyst in a liquid reaction composition containing an organic solvent composed of methanol, methyl iodide, acetic acid and/or methyl acetate and water to a small content ratio and blowing carbon monoxide gas into the liquid reaction composition with a solid catalyst concentration of not less than 100 kg/m$^3$ in terms of the reaction volume;

a first separation step of separating and taking out the liquid reaction composition and off gas from said reaction step;

a second separation step of conducting an operation of flash evaporation by introducing the liquid reaction composition separated in the first separation step into a flash vessel and thereby separating a gaseous fraction flowing out from an upper tower section and a liquid fraction flowing out from a lower tower section;

a third separation step of leading the gaseous fraction separated in said second separation step into a distillation system and separating off gas, a product acetic acid fraction, a heavy fraction and a circulating fraction;

a circulation step of returning the liquid fraction separated in said second separation step and the circulating fraction separated in said third separation step to the reactor;

a first absorption step of conducting an operation of gas absorption for the off gas separated in said first separation step, using methanol as absorbent liquid;

a second absorption step of conducting an operation of gas absorption for the off gas separated in said third separation step, using methanol as absorbent liquid under a pressure lower than that of said first absorption step; and an exhaustion step of exhausting the off gas left after said first absorption step, the off gas left after said second absorption step and the heavy fraction separated in said third separation step to the outside of the system; and the methanol that is regulated for temperature to 10 to 25° C. is used as absorbent liquid in said first and second absorption steps and divided so as to use 50 to 80 wt % of the entire methanol to be used in the two absorption steps in said second absorption step and the methanol left after the two absorption steps is used as raw material methanol in the reaction step.

20. A method according to claim 18 or 19, wherein the solid catalyst is formed by causing a quaternary pyridine resin to carry rhodium carbonyl complex.

21. A method according to claim 18 or 19, wherein methanol is divided so as to use 55 to 70 wt % of the entire methanol to be used in the two absorption steps in said second absorption step.

* * * * *